US009486131B2

(12) United States Patent
Mathaneswaran et al.

(10) Patent No.: US 9,486,131 B2
(45) Date of Patent: Nov. 8, 2016

(54) APPARATUS FOR SURGERY

(75) Inventors: Vickneswaran Mathaneswaran, Kuala Lumpur (MY); Hong Guan Ng, Perak (MY)

(73) Assignee: UNIVERSITI MALAYA, Kuala Lumpur (MY)

( * ) Notice: Subject to any disclaimer, the term of this patent is extended or adjusted under 35 U.S.C. 154(b) by 54 days.

(21) Appl. No.: 13/259,488

(22) PCT Filed: Jun. 3, 2009

(86) PCT No.: PCT/MY2009/000067
§ 371 (c)(1),
(2), (4) Date: Sep. 23, 2011

(87) PCT Pub. No.: WO2010/110641
PCT Pub. Date: Sep. 30, 2010

(65) Prior Publication Data
US 2012/0035638 A1 Feb. 9, 2012

(30) Foreign Application Priority Data
Mar. 26, 2009 (MY) ................ PI20091229

(51) Int. Cl.
*A61B 1/32* (2006.01)
*A61B 17/02* (2006.01)

(52) U.S. Cl.
CPC .............. *A61B 1/32* (2013.01); *A61B 17/02* (2013.01); *A61B 17/0218* (2013.01)

(58) Field of Classification Search
CPC .............. A61B 17/0218; A61B 17/0206
USPC ................. 600/201–235
See application file for complete search history.

(56) References Cited

U.S. PATENT DOCUMENTS

| | | | | |
|---|---|---|---|---|
| 3,851,642 A | * | 12/1974 | McDonald | 600/212 |
| 4,300,541 A | * | 11/1981 | Burgin | 600/213 |
| 4,889,112 A | * | 12/1989 | Schachner | A61B 17/2812 128/200.26 |
| 5,014,407 A | * | 5/1991 | Boughten | B25B 7/02 29/235 |
| 5,320,611 A | | 6/1994 | Bonutti et al. | |
| 5,498,231 A | | 3/1996 | Franicevic | |
| 5,569,300 A | * | 10/1996 | Redmon | 606/207 |
| 5,785,648 A | * | 7/1998 | Min | 600/206 |
| 6,096,046 A | * | 8/2000 | Weiss | A61B 17/0206 600/210 |
| 6,287,322 B1 | * | 9/2001 | Zhu | A61B 17/0057 606/108 |
| 6,425,901 B1 | * | 7/2002 | Zhu et al. | 606/142 |

(Continued)

FOREIGN PATENT DOCUMENTS

| | | |
|---|---|---|
| WO | 9922637 | 5/1999 |
| WO | 2006050047 | 5/2006 |
| WO | 2006074237 | 7/2006 |

*Primary Examiner* — Jan Christopher Merene
*Assistant Examiner* — Atiya Mahmud
(74) *Attorney, Agent, or Firm* — Preston Smirman; Smirman IP Law, PLLC

(57) ABSTRACT

An apparatus for surgery includes a first arm member and a second arm member movable in relation to one another in a same plane through a pivoted portion, in an open and closed position, that is controlled by a pair of handles; at least one through hole is made onto one of the arm members; and a first blade and a second blade, each defined by a tip, a body and a base, perpendicularly extended in parallel from the first and second arm members respectively; wherein both blades have a substantially flat portion started from the tip to the body followed by an expanded portion around the base attached on the arm members that the expanded portion defines a groove therein enclosing the through hole in the closed position.

5 Claims, 5 Drawing Sheets

(56) References Cited

U.S. PATENT DOCUMENTS

| | | | |
|---|---|---|---|
| 6,432,048 B1* | 8/2002 | Francois | 600/220 |
| 7,189,234 B2* | 3/2007 | Zucherman et al. | 606/249 |
| 7,666,201 B2* | 2/2010 | Grayzel et al. | 606/174 |
| 8,603,130 B2* | 12/2013 | Grayzel | A61B 17/02 606/151 |
| 2003/0069477 A1* | 4/2003 | Raisman et al. | 600/220 |
| 2004/0024291 A1 | 2/2004 | Zinkel | |
| 2005/0070765 A1 | 3/2005 | Abdelgany et al. | |
| 2005/0080320 A1* | 4/2005 | Lee et al. | 600/214 |
| 2005/0192482 A1* | 9/2005 | Carpenter et al. | 600/203 |
| 2005/0234304 A1* | 10/2005 | Dewey et al. | 600/210 |
| 2005/0273133 A1 | 12/2005 | Shluzas et al. | |
| 2006/0052672 A1* | 3/2006 | Landry et al. | 600/233 |
| 2006/0063978 A1* | 3/2006 | Ritland | A61B 17/02 600/213 |
| 2007/0027364 A1* | 2/2007 | Schwer | 600/219 |
| 2007/0123753 A1* | 5/2007 | Abdelgany et al. | 600/220 |
| 2008/0004630 A1 | 1/2008 | Badie | |
| 2008/0146885 A1* | 6/2008 | Protopsaltis | 600/210 |
| 2008/0214898 A1* | 9/2008 | Warren | 600/210 |
| 2009/0203969 A1* | 8/2009 | Cohen et al. | 600/245 |

\* cited by examiner

APPARATUS FOR SURGERY

CROSS-REFERENCE TO RELATED APPLICATION

The instant application claims priority to Malaysian Patent Application No. Pl 20091229, filed Mar. 26, 2009, pending, and PCT International Application No. PCT/MY2009/000067, filed on Jun. 3, 2009, pending, the entire specifications of both of which are expressly incorporated herein by reference.

FIELD OF INVENTION

The present invention relates to an apparatus to be used for surgery. In more specific, the disclosed apparatus is capable of expanding to create a tunnel thereto in soft tissues for performing endoscopic surgery upon deployment of the apparatus.

BACKGROUND OF THE INVENTION

Current endoscopic operation especially with soft tissue is performed using a tube system containing two or more inbuilt channels. Through these inbuilt channels, the rod lens camera system, the light source and the endoscopic working instruments are introduced into the site for carrying out the operation. Though it has been used for years, persistent shortcomings are found to be significantly affecting efficiency of the operation conducted through this system. For example, miniaturization of the working instruments in such system has taken toll on its efficiency in operation in contrast to microsurgery especially in removing tumors and the similar lesion. Furthermore, parallel introduction of the working instrument, camera and light source in a single tube has limited functionality of each component to act independently for operation. Moreover, movement of the entire tube in delicate soft tissue like brain tissue may prone to inflict additional damages to the patients as well. Therefore, a new instrument with features obviating the above mentioned disadvantages is needed.

International Patent publication no. 2006050047 discloses an apparatus for accessing brain tissue. The disclosed apparatus mainly comprises an obturator and cannula assembly including a dilating obturator having an a traumatic dilating tip, an optical window and a shaft portion, while the cannula disposed around the dilating obturator shaft portion. The invention is claimed to be less invasive compared to the conventional apparatus yet an additional stylet with navigation array for image guidance is required to be initially inserted as a pilot before the actual cannula is deployed.

A multiple tract cannula system is provided in United State patent with publication no. 2008004630. The disclosed system is a tubular extension having multiple attachment members attached and protruded out from the exterior surface of the tubular extension in different direction. The attachment member is used to contact and deliver therapeutic agent to the brain tissue.

Zinkel has filed a patent with publication no. 2004024291 claiming an apparatus for spinal surgery which capable of minimizing tissue trauma in the surgery. This invention is not suitable to be used for soft delicate tissue like brain. As the deployment of this invention do provide a large channel for operation, however, the tunnel itself is not enclosed to avoid injuries inflicted onto the delicate brain tissue caused by the inserted working instruments. Furthermore, it lacks of other feature such as means to hold the light source or camera that can greatly improve convenience in conducting the surgery.

Another U.S. patent application Ser. No. 5,320,611 discloses an expandable cannula for surgery having longitudinal wires circumferentially surrounded by an elastic sheath. The longitudinal wires of the disclosed invention are expandable radially outwardly upon insertion of a dilator and retract its original size upon removal of the dilator caused by the contract of the elastic sheath.

SUMMARY OF THE INVENTION

The present invention aims to provide an apparatus for performing endoscopic surgery that it can minimize tissue invasion by reducing the opened incision for deployment of the working instruments.

Further object of the present invention is to offer maximized visualization and access to the surgical field which significantly improve efficiency of the surgery.

The present invention also aims to provide additional protection to delicate soft tissue like brain while conducting endoscopic surgery through the disclosed apparatus.

At least one of the preceding objects is met, in whole or in part, by the present invention, in which one of the embodiment of the present invention includes an apparatus for surgery comprising a first arm member and a second arm member movable in relation to one another in a same planar through a pivoted portion, in an open and close position, which is controlled by a pair of handle; at least one through hole are made onto one of the arm member; and a first blade and a second blade, each defined by a tip and a body as well as a base, perpendicularly extended in parallel from the first and second arm members respectively; wherein both blades have substantially flat portion started from the tip to the body followed by an expanded portion around the base attached on the arm member that the expanded portion defines a groove therein enclosing the through hole in the close position. This can be made from Titanium, plastic or surgical steel For endoscopic surgery of delicate soft tissue, a elastic sleeve wraps and encloses the first and second blades circumferentially to be expandable forming a tunnel in the open position. The tunnel created in such a way prevents unwanted injuries to the surrounding soft tissue caused by the inserted working instrument Another major embodiment of the present invention is an apparatus for surgery comprising a first arm member and a second arm member movable in relation to one another in a same planar through a pivoted portion, in an open and close position, which is controlled by a pair of handle; a first blade and a second blade, each defined by a tip and a body as well as a base, perpendicularly extended in parallel from the first and second arm members respectively; a elastic sleeve wrapped and enclosed the first and second blades around the tips and the bodies to be expandable forming a tunnel in the open position; wherein the sleeve is expandable to form a tunnel in the open position of the apparatus.

To endoscopic surgery of brain, neuronavigation technique may be employed thus a navigating means may be incorporated in one embodiment to allow the disclosed apparatus to be recognized and tracked or even maneuvered by a tracking device during the operation.

Another aspect of the present invention may include the first and second blades which are demountably engaged onto the first and second arm member respectively.

Still another aspect of the present invention to have the first and/or second blades made to be illuminative partially or wholly thus eliminates the need of external light source.

When an external light source and/or camera system is used in the operation, these instruments are preferably secure stably to yield a good visualization. The present invention provides a holding means incorporated to secure these instruments to be inserted into the through hole.

One aspect of the present invention further comprises a receiving means mounted on the pivoted portion to provide a site of attachment of clamps and/or navigation array.

DETAILED DESCRIPTION OF THE INVENTION

It is to be understood that the present invention may be embodied in other specific forms and is not limited to the sole embodiment described herein. However modification and equivalents of the disclosed concepts such as those which readily occur to one skilled in the art are intended to be included within the scope of the claims which are appended thereto.

It is important to be noted that the embodiments described herein are used preferably in operation of delicate soft tissue especially brain tissue. Moreover, the disclosed apparatus is applicable in operation treating lesion found as inner as parenchyma of the brain. Nonetheless, the disclosed apparatus can be employed as well in operation for other parts or organs and not limited solely for brain.

Figure 1:
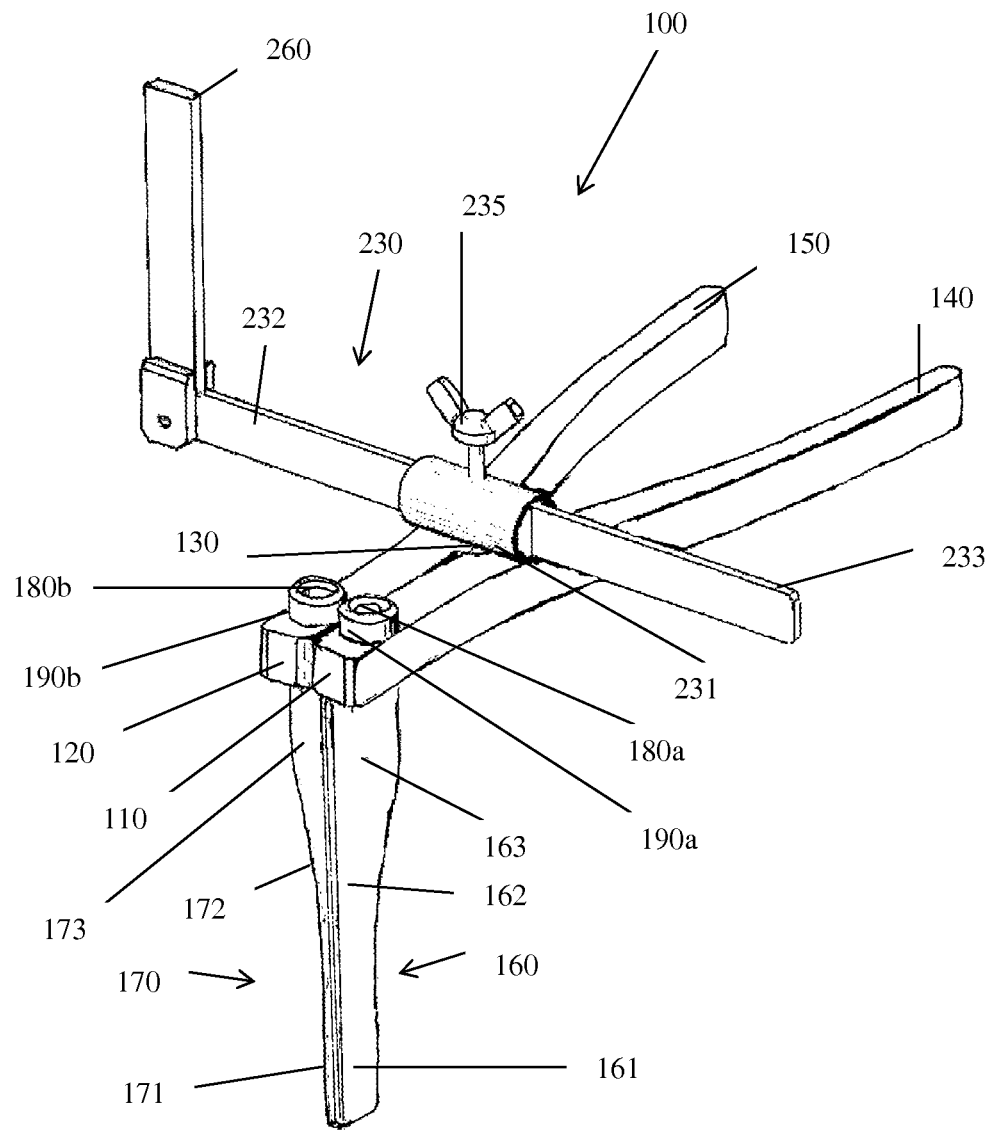
FIG. 1 is a perspective view of one embodiment of the present invention.
Figure 2:
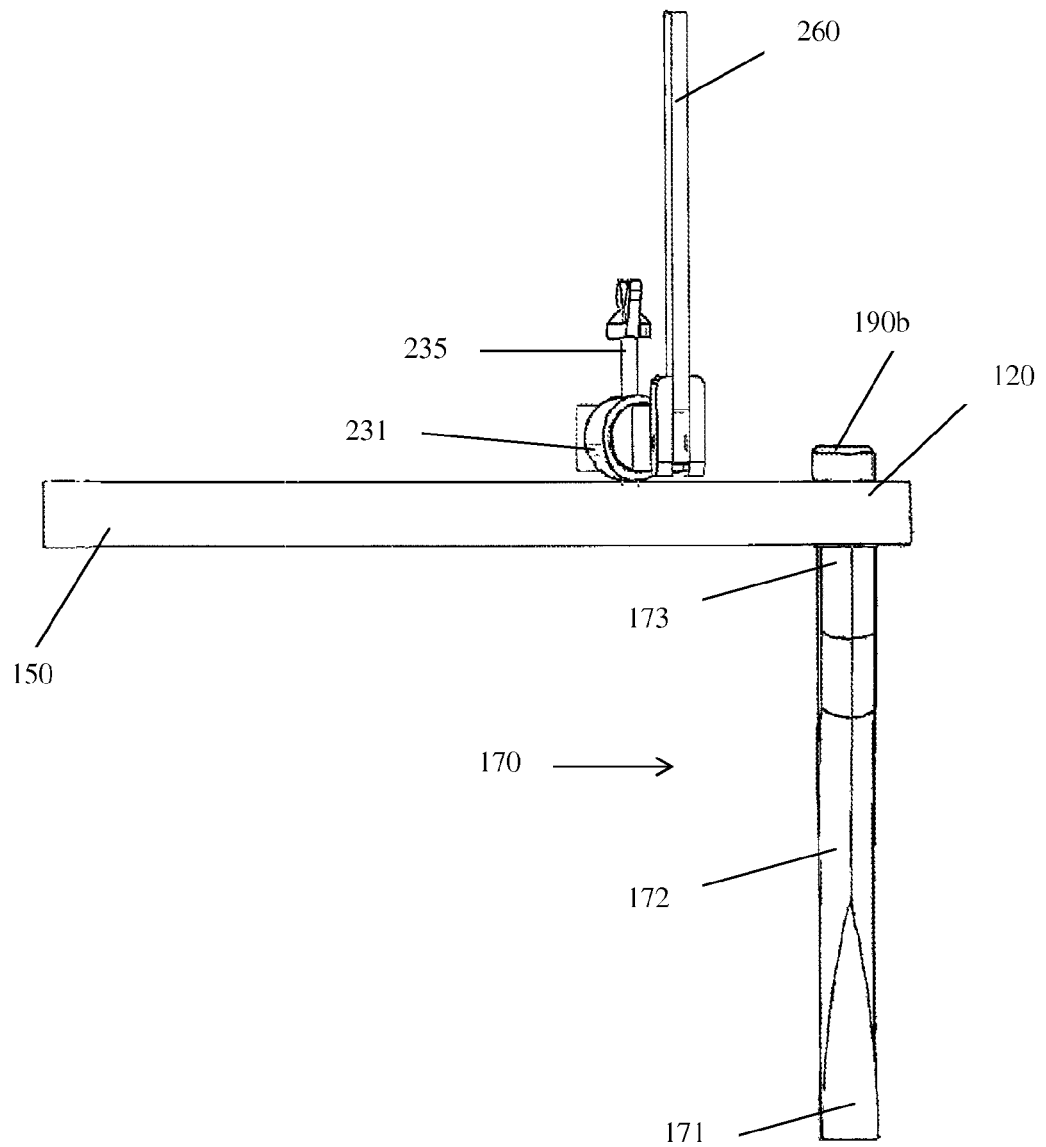
FIG. 2 is a side view of embodiment shown in FIG. 1.

The first embodiment of the present invention is an apparatus (100), as presented in FIGS. 1 and 2, to be used for surgery, comprises a first arm member (110) and a second arm member (120) movable in relation to one another in a same plane through a pivoted portion (130), in an open and closed position, that is controlled by a pair of handles (140 and 150); a first blade (160) and a second blade (170), each defined by a tip (161 or 171), a body (162 or 172) and a base (163 or 173), perpendicularly extended in parallel from the first (110) and second arm members (120) respectively; an elastic sleeve (400) wrapped and enclosed circumferentially the first (160) and second blades (170); wherein the sleeve (400) is expandable to form a tunnel in the open position of the apparatus (100).

Still a second preferred embodiment of the apparatus comprises a first arm member (110) and a second arm member (120) movable in relation to one another in a same plane through a pivoted portion (130), in an open and closed position, that is controlled by a pair of handles (140 and 150); at least one through hole (180a or 180b) is made onto one of the arm members (110 or 120); and a first blade (160) and a second blade (170), each defined by a tip (161 and 171), a body (162 and 172) and a base (163 and 173), perpendicularly extended in parallel from the first (110) and second arm members (120) respectively; wherein both blades (160 and 170) have a substantially flat portion started from the tip (161 and 171) to the body (162 to 172) followed by an expanded portion around the base (163 and 173) attached on the arm members (110 and 120) that the expanded portion defines a groove therein enclosing the through hole (180a or 180b) in the closed position.

The blades of the second embodiments has an enlarged or expanded base portion (163 or 173) attached onto the respective arms (110 or 120) where each attached base portion surrounds the rim of the through hole (180a or 180b) available on the respective arm partially. In the close position of the disclosed apparatus, the one or more through holes are fully surrounded by the rim of the base portions (163 and 173) of the two blades (160 and 170). Further, in the close position, a groove is substantially defined within the base portions. The expanded base portions of the present invention allow working instruments entering the created tunnel conveniently via the through holes during operation. In the more preferred embodiment, the tips and the rest of the body of the blades are flattened so that these portions of the blades are tightly contacting one another in the elongate surface thus these portion of the apparatus can be inserted through a relatively smaller incision made. Yet, it is possible to made the tips or even part of the bodies to be curvature or expanded to employ the present invention for different application.

Figure 3:
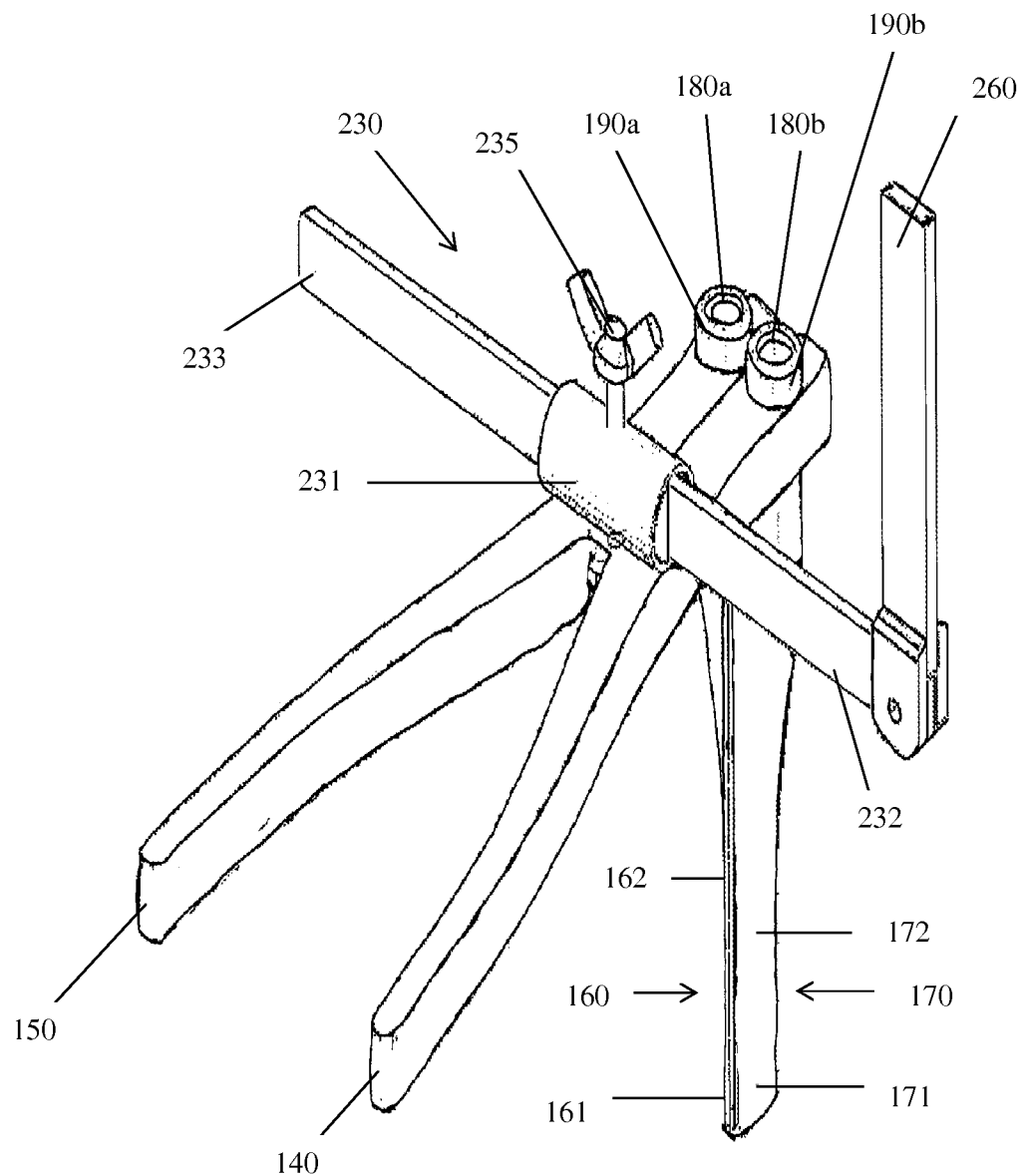
FIG. 3 is another top perspective view of the embodiment shown in FIG. 1.

According to the second embodiment as in the foregoing description, the lighting the through holes (180a and 180b) made onto the arms (110 and 120) provide a site for insertion or anchorage of the, preferably, lens camera system and/or external light source. The lens camera system or light source is inserted into the created tunnel via the through hole during the operation and can be anchored onto the through holes (180a and 180b) to relieve the user hands from holding the instruments. Light of various wavelengths could also be used to allow the identification of tumors from normal tissue To stably hold these instruments, the disclosed apparatus further comprise holding means (180) incorporated to secure the anchored instrument as shown in FIG. 3. In the shown embodiment, the holding means (190a or 190b) is screw caplike device, having a bore on top to let the instruments penetrating through, which can be mounted on threaded protrusion surrounding the rim of the through holes (180a and 180b) on the arm surface opposite to the blades (160 and 170). Once placing the instrument at the desired location, the holding means (190a and 190b) are mounted onto and turn clockwise or anti-clockwise against the threaded protrusion to tighten and secure the instruments.

In respect to the second embodiment, an elastic sleeve (400) is employed to wrap and enclose the first (160) and second blades (170) that the elastic sleeve (400) is expandable forming a tunnel in the open position of the disclosed apparatus as identical to the first embodiment. The formed tunnel is an important feature found in the present invention to achieve the above mentioned objects and advantages. Through the formed tunnel, different working instruments of significant size such as micro-dissectors, standard steel suction tubes, conventional slim bipolar forceps and the like which can not be deployed by conventional methods now can be employed to work on the surgical site. The inserted working instruments have shown better efficiency in conducting the surgery in contrast to conventional endoscopy tube systems. The working instruments can work independently without hindering one another compared to conventional systems.

Owing to its elasticity, the sleeve (400) is in a contracted state forming only a thin sheath when it is wrapped around the first (160) and second blades (170) in the closed position of the disclosed apparatus. Thus, only a small incision is needed to be made on the soft tissue in order to deploy the blades with the sleeve (400) while the apparatus maintains its closed position. Once inserted, only then the apparatus shifts to the open position to depart the blades followed by expansion of the sleeve (400) to form a tunnel thereto. Hence, the damage inflicted onto the tissue is minimized by the present invention as opposed to conventional approaches which require a relatively larger incision for insertion of the tube system. Further, the expanded sleeve (400) also provides a protective shield for the surrounding soft tissue at the surgical site possibly caused by movement of the working instrument.

In accordance with the preferred embodiment, the disclosed apparatus may comprise a navigating means that allow the apparatus to be recognized and tracked by a tracking device. Specifically, the navigating means can be a neuronavigation antenna allowing the disclosed apparatus to be recognized and tracked by a navigation tracking camera.

Incorporation of the navigating means allows the user of the present invention to plan the trajectory for the deployment of the disclosed apparatus to avoid unnecessary contact with critical structures positioned around the surgical site. The navigating feature also permits the user to access the surgical site at a strategic planar, for example, entering the hematoma along the long axis.

Figure 4:
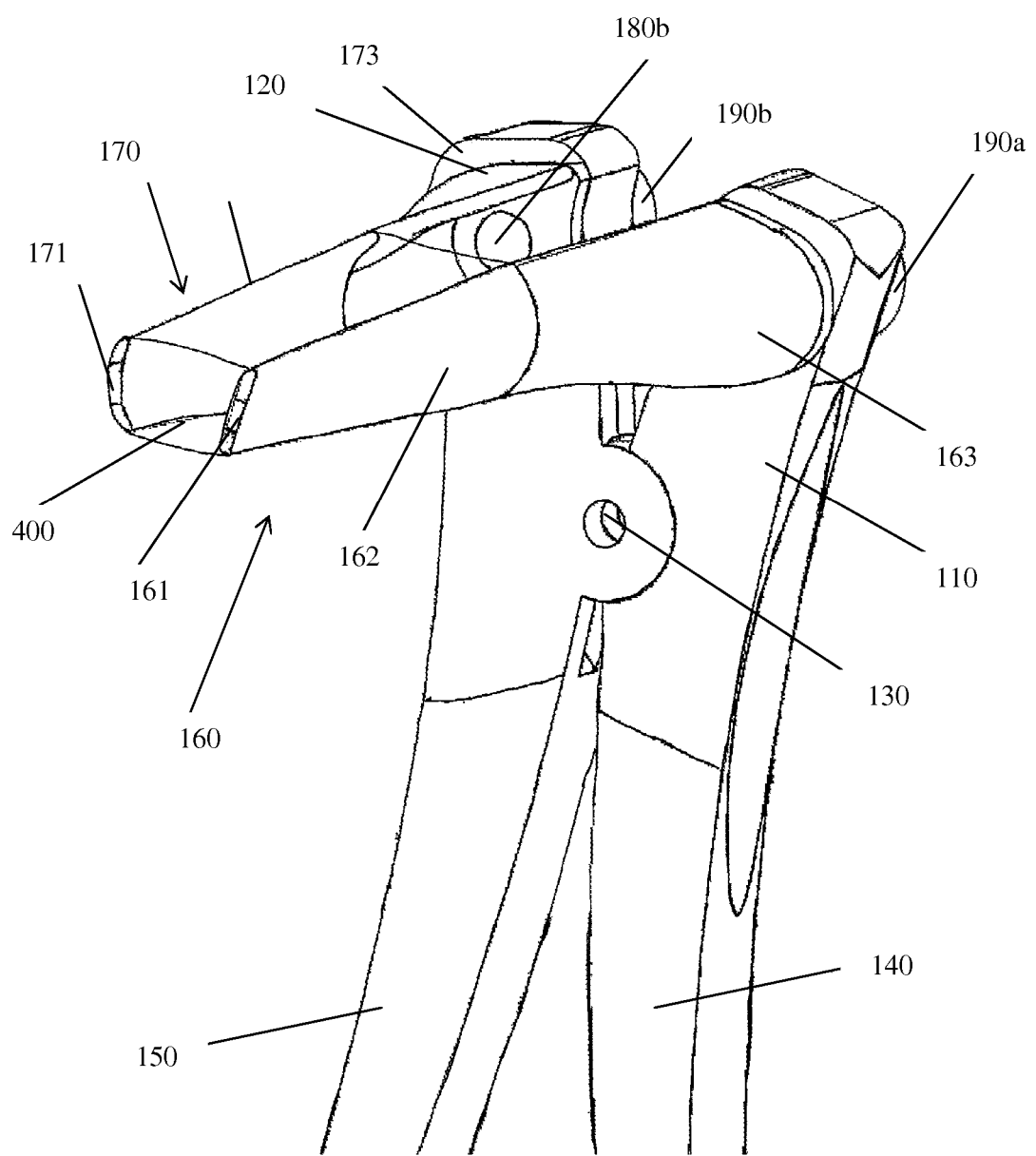
FIG. 4 shows the enlarged front view of the embodiment in FIG. 1 without mounting of the receiving means.
Figure 5:
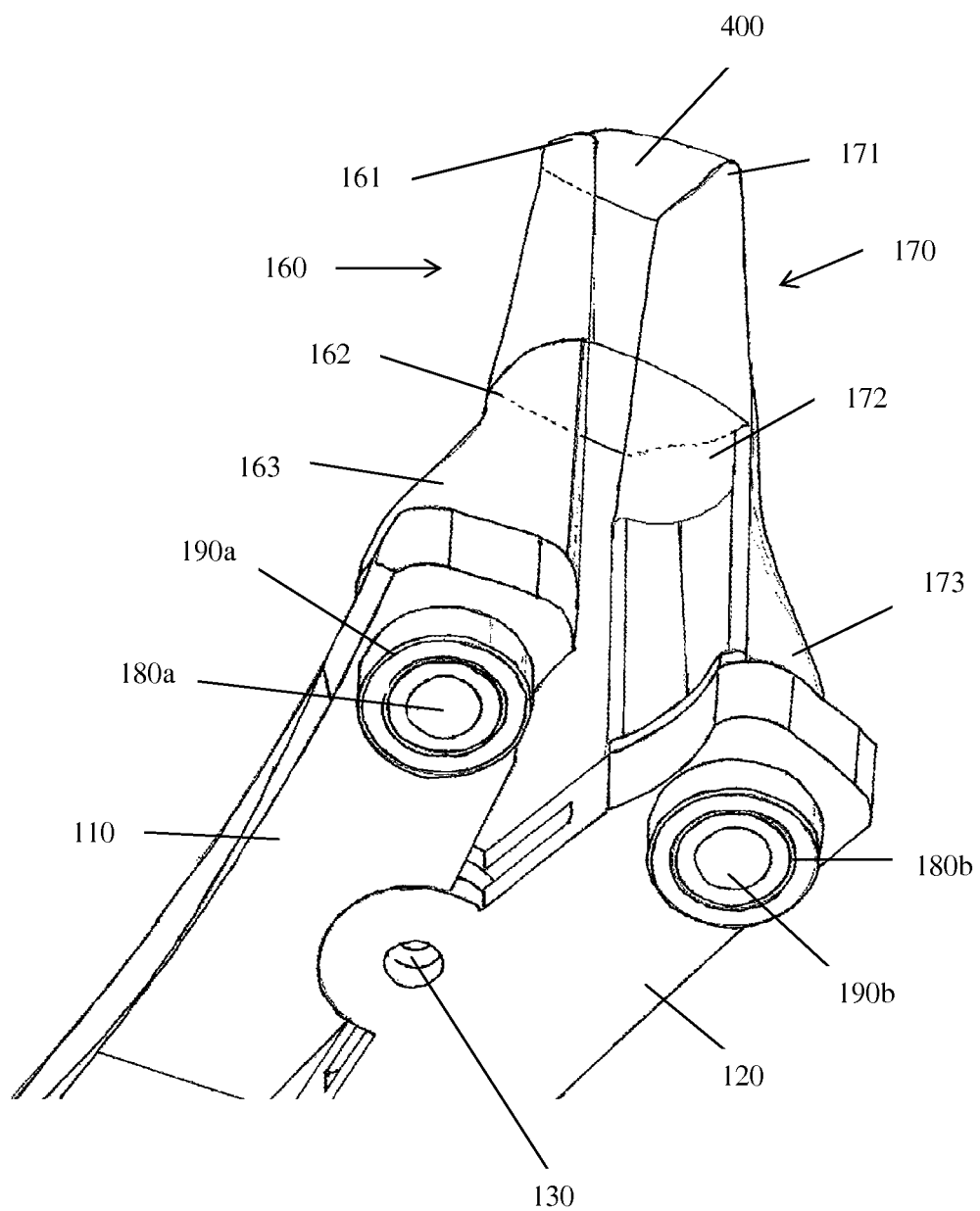
FIG. 5 shows enlarged back view of the disclosed apparatus around arm members without mounting of the receiving means.

As shown in FIGS. 4 and 5, it clearly reveals that both the first blade (160) and the second blade (170) are attached onto the first arm (110) and second arm (120) respectively through the base portion. Preferably, the blades are made to be demountably engaged at the base portion. Both blades, in this embodiment, can be fixed onto the respective arms by fastening means such as screw, nuts, and the like that the blades can be detached from the arms upon undoing the fastening means. Moreover, a simple male and female attachment mechanism can be employed to achieve the temporary mounting rather than applying the fastening means. Consequently, the user can change blades of different length or size for different application or surgical sites to optimize efficacy of the operation.

It is preferable to reduce number of unnecessary working instrument to be inserted into the created tunnel to acquire bigger space and movement freedom of other tools in the tunnel for performing the operating procedures. Consequently, in one embodiment, the first (160) and/or second blades (170) of the disclosed apparatus are partially or wholly made to be illuminative to eliminate the need of external light source. For example, the blades may be made from light-permitting material such as glass or plastic further embedded with optical fiber. Upon connecting to a power source, the embedded optical fibers shall generate light thereon and eliminating the need of using external light source.

To stably hold the disclosed apparatus in position for preventing accidental motion as operations are being carried out, a receiving means is mounted on the apparatus. Preferably, the receiving means (230) has a center piece (231) to be fixed on the pivoted portion (130) of the disclosed apparatus. At least a pair of elongate protrusions (232 and 233) extends out laterally from the center piece (230), preferably, perpendicular to the center axis of the disclosed apparatus and transverses the planar surface. The elongate protrusions (232 and 233) provide a site to receive clamps and the like for holding and securing the disclosed apparatus at the desired position during the operation. Nonetheless, other useful tools such as navigation array can be attached onto the protrusions (232 and 233) as well.

Pursuant to another preferred embodiment, the elongate protrusions (232 and 233) is a single plate which can slide or glide through a hollow passage provided in the center piece (231) and the plate can be locked against onto the center piece (231) through a fixing means (235) found on the center piece (231). The slidable plate allows user to customize the length of the protrusions (232 and 233) upon their preference. Particularly, the center piece (231) is fabricated to contain a hollow passage large enough for fitting in the short edge of the plate or the center piece (231) is simply made of a hollow tube with a threaded hole available on the top of the center piece (231). The threaded hole interconnects, preferably transverse to, the hollow passage, while the fixing means (235) can be a wing screw to be inserted into the threaded hole. After adjusting the length of the protrusion (231 and 232), the wing screw is turned into the threaded hole to press the plate against the inner surface of the center piece thus locking the plate thereon and the plate is movable again once loosen the wing screw. The center piece (231) and the extending protrusion (232 and 233) are removably attached onto the disclosed apparatus as in FIGS. 4 and 5.

The present disclosure includes as contained in the appended claims, as well as that of the foregoing description. Although this invention has been described in its preferred form with a degree of particularity, it is understood that the present disclosure of the preferred form has been made only by way of example and that numerous changes in the details of construction and the combination and arrangements of parts may be resorted to without departing from the scope of the invention.

The invention claimed is:

1. An apparatus for surgery in an operation treating a lesion found in a brain, comprising:
a first arm member and a second arm member movable in relation to one another through a pivoted portion to assume an open and closed position, wherein the first and second arm members are controlled by a pair of handles;
an area defining a first through hole formed on an area proximate to a terminal portion of the first arm member and a second through hole formed on an area proximate to a terminal portion of the second arm member;
a first blade and a second blade, each defined by a tip, a body and a base, perpendicularly extending, in parallel, away from the terminal portions of the first and second arm members, respectively;
wherein the first through hole is axially aligned with the first blade member along an entire length of the first through hole;
wherein the second through hole is axially aligned with the second blade member along an entire length of the second through hole;
an elastic sleeve wrapping and enclosing the first and second blades so as to be expandable and form a tunnel when in the open position;
wherein, on an inner surface of the first and second blades, there is formed a substantially flat portion started from the tip to the body followed by an enlarged base portion attached on the first and second arm members, wherein, on an outer surface of the tip of the first and second blades, there is formed a substantially flat portion, wherein the enlarged base portions of the first and second blades define a groove therein enclosing the first and second through holes when in the closed position;

wherein a major portion of an inner surface of the tip and body of the first and second blades are flush against one another when in the closed position;

a receiving system mounted on the pivoted portion to provide at least one attachment site for clamps and a navigation array;

wherein the receiving system includes a receiving member fixed on the pivoted portion and having an area defining a bore formed therein; and at least one elongated member operably associated with the receiving member;

wherein the elongated member extends laterally outwardly away from the bore.

2. The apparatus according to claim 1, wherein at least one of the first and second blades is demountably engaged onto at least one of the first and second arm members.

3. The apparatus according to claim 1, wherein at least one of the first and second blades are at least partially illuminative.

4. The apparatus according to claim 1, further comprising a holding system formed on the terminal portions of the first and second arm members and being proximate to the first and second through holes, wherein the holding system is operable to secure an instrument inserted into the first or second through holes.

5. The apparatus according to claim 1, wherein the enlarged base portion has a C-shaped cross-section.

* * * * *